United States Patent
Akagane (10) Patent No.: US 11,179,174 B2
(45) Date of Patent: Nov. 23, 2021

(54) HIGH-FREQUENCY TREATMENT INSTRUMENT AND END EFFECTOR

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 395 days.

(21) Appl. No.: 16/047,394

(22) Filed: Jul. 27, 2018

(65) Prior Publication Data

US 2018/0368879 A1    Dec. 27, 2018

Related U.S. Application Data

(63) Continuation of application No. PCT/JP2016/052713, filed on Jan. 29, 2016.

(51) Int. Cl.
*A61B 17/32* (2006.01)
*A61B 18/12* (2006.01)
(Continued)

(52) U.S. Cl.
CPC ...... *A61B 17/320092* (2013.01); *A61B 18/12* (2013.01); *A61B 18/1442* (2013.01);
(Continued)

(58) Field of Classification Search
CPC ............ A61B 17/320092; A61B 18/12; A61B 18/1442; A61B 2017/320094; A61B 2017/320095; A61B 2017/320093; A61B 2018/00077; A61B 2018/0013; A61B 2018/00148; A61B 2018/1457; B05D 3/0281; B05D 5/08; A61L 2300/104; A61L 2420/02
(Continued)

(56) References Cited

U.S. PATENT DOCUMENTS 5,385,679 A    1/1995    Uy et al.
5,520,180 A    5/1996    Uy et al.
(Continued)

FOREIGN PATENT DOCUMENTS

EP    0 542 294 A1    5/1993
EP    2 620 482 A1    7/2013
(Continued)

OTHER PUBLICATIONS

Jul. 31, 2018 International Preliminry Report on Patentability issued in Iinternational Patent Application No. PCT/JP2016/052713.
(Continued)

*Primary Examiner* — Linda C Dvorak
*Assistant Examiner* — Nils A Potter
(74) *Attorney, Agent, or Firm* — Oliff PLC (57) ABSTRACT

In an end effector of a high-frequency treatment instrument, a coating covers an outer surface of an electrode, and formed from a conductive mixture obtained by mixing a non-conductive material and a conductive material. The conductive material contained in the mixture includes first elements and second elements, and each of the first elements has a shape with a higher flatness quotient than each of the second elements.

11 Claims, 5 Drawing Sheets

(51) Int. Cl.
  *A61B 18/14* (2006.01)
  *B05D 3/02* (2006.01)
  *A61B 18/00* (2006.01)
  *B05D 5/08* (2006.01)
(52) U.S. Cl.
  CPC ...................... *B05D 3/0281* (2013.01); *A61B 2017/320093* (2017.08); *A61B 2017/320094* (2017.08); *A61B 2017/320095* (2017.08); *A61B 2018/0013* (2013.01); *A61B 2018/00077* (2013.01); *A61B 2018/00148* (2013.01); *A61B 2018/1457* (2013.01); *A61L 2300/104* (2013.01); *A61L 2420/02* (2013.01); *B05D 5/08* (2013.01)
(58) Field of Classification Search
  USPC .......................................................... 606/45
  See application file for complete search history.

(56) References Cited

U.S. PATENT DOCUMENTS

| | | | |
|---|---|---|---|
| 5,536,446 A | | 7/1996 | Uy et al. |
| 2002/0043654 A1 | | 4/2002 | Karttunen et al. |
| 2003/0195513 A1* | 10/2003 | Truckai .............. A61B 18/1442 606/51 |
| 2005/0267464 A1* | 12/2005 | Truckai .............. A61B 18/1442 606/41 |
| 2006/0229601 A1 | | 10/2006 | Swoyer et al. |
| 2009/0216157 A1* | 8/2009 | Yamada ......... A61B 17/320092 601/2 |
| 2013/0175899 A1 | | 7/2013 | Kato et al. |
| 2015/0044488 A1* | 2/2015 | Nesbitt .................. A47J 36/025 428/474.4 |
| 2015/0231308 A1* | 8/2015 | Koullick ................ A61L 29/08 604/509 |
| 2015/0320437 A1* | 11/2015 | Worrell .................... A61N 7/00 606/169 |

FOREIGN PATENT DOCUMENTS

| | | |
|---|---|---|
| JP | S62-152705 U | 9/1987 |
| JP | H03-75053 A | 3/1991 |
| JP | H04-307055 A | 10/1992 |
| JP | 2010-227462 A | 10/2010 |
| JP | 5836543 B1 | 12/2015 |

OTHER PUBLICATIONS

May 29, 2020 Chinese Office Action issued in Chinese Patent Application No. 201680080172.1.

Apr. 26, 2016 Search Report issued in linternational Patent Application No. PCT/JP2016/052713.

Jul. 12, 2019 Extended European Search Report issued in European Patent Application No. 16887970.8.

* cited by examiner

HIGH-FREQUENCY TREATMENT INSTRUMENT AND END EFFECTOR

CROSS-REFERENCE TO RELATED APPLICATIONS

This is a Continuation Application of PCT Application No. PCT/JP2016/052713, filed Jan. 29, 2016, the entire contents of which are incorporated herein by reference.

BACKGROUND OF THE INVENTION

1. Field of the Invention

The present invention relates to a high-frequency treatment instrument including an electrode for applying a high-frequency current to the target of treatment. Further, the present invention relates to an end effector provided in this high-frequency treatment instrument.

2. Description of the Related Art

JP Pat. Appln. KOKAI Publ. No. 2010-227462 discloses a high-frequency treatment instrument that applies a high-frequency current to the target of treatment through the outer surface by supplying high-frequency electric energy. The outer surface of the electrode in this high-frequency treatment instrument is covered with a coating. The coating is formed from a mixture of a low-adhesive material (non-conductive material), such as a fluorine resin, that is non-susceptible to adhering to living tissue and a conductive material such as aluminum. Adhesion of the target of treatment to the electrode is prevented by using a low-adhesive material for coating.

BRIEF SUMMARY OF THE INVENTION

According to one aspect of the invention, a high-frequency treatment instrument including: an end effector configured to treat a target of treatment; and a housing which supports the end effector, and which is held by an operator; wherein the end effector includes: an electrode having an outer surface, the electrode being configured to apply, by being supplied a high-frequency electric energy to the electrode, a high-frequency electric current to the target of treatment through the outer surface; and a coating which covers at least part of the outer surface of the electrode, the coating being formed from a mixture obtained by mixing a non-conductive material and a conductive material, the conductive material contained in the mixture being at a smaller ratio than the non-conductive material, the conductive material contained in the mixture including first elements and second elements, each of the first elements having a shape with a higher flatness quotient than each of the second elements, the first elements in the mixture being at a smaller ratio than the second elements so that the coating ensures large electrostatic capacitance and decreases impedance in circuits where the high-frequency current passes through, and thereby the coating being conductive with respect to the high-frequency current.

According to one another aspect of the invention, an end effector including: an electrode having an outer surface, the electrode being configured to apply, by being supplied a high-frequency electric energy to the electrode, a high-frequency electric current to a target of treatment through the outer surface; and a coating which covers at least part of the outer surface of the electrode, the coating being formed from a mixture obtained by mixing a non-conductive material and a conductive material, the conductive material contained in the mixture being at a smaller ratio than the non-conductive material, the conductive material contained in the mixture including first elements and second elements, each of the first elements having a shape with a higher flatness quotient than each of the second elements, the first elements in the mixture being at a smaller ratio than the second elements so that the coating ensures large electrostatic capacitance and decreases impedance in circuits where the high-frequency current passes through, and thereby the coating being conductive with respect to the high-frequency current.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
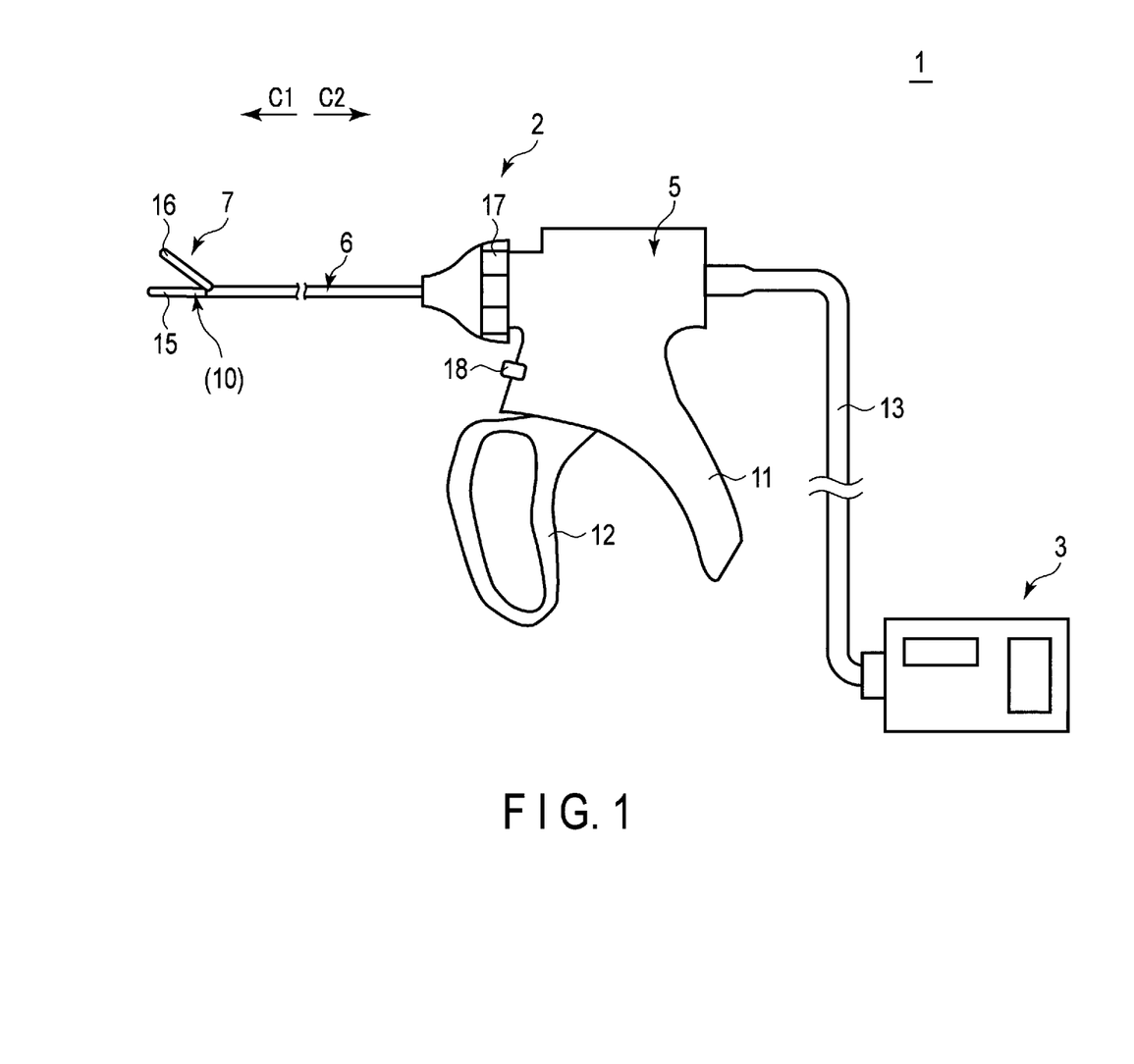
FIG. 1 is a schematic diagram showing a treatment system according to a first embodiment.

The first embodiment of the present invention will be described with reference to FIGS. 1-8. FIG. 1 is a diagram showing a treatment system 1 according to the aforementioned embodiment. As shown in FIG. 1, the treatment system 1 includes a high-frequency treatment instrument 2 and an energy control device 3 that controls the energy supply to the high-frequency treatment instrument 2. In FIG.

1, the arrow C1 side is the distal side and the arrow C2 side (opposite side to the distal side) is the proximal side.

The high-frequency treatment instrument 2 includes a housing 5 capable of being held, a shaft 6 connected to the distal side of the housing 5, and an end effector 7 provided in the distal portion of the shaft 6. The housing 5 is provided with a grip 11, and a handle 12 is rotatably attached to the housing 5. As the handle 12 rotates relative to the housing 5, the handle 12 opens or closes with respect to the grip 11.

The end effector (treatment section) 7 configured to treat a target of treatment such as living tissue is provided in the distal side part of the high-frequency treatment instrument 2. In the aforementioned embodiment, the end effector 7 includes a first gripping piece 15 and a second gripping piece 16. By opening or closing the handle 12 with respect to the grip 11, the space between the pair of gripping pieces 15, 16 opens or closes. By closing the space between the pair of gripping pieces 15, 16, it becomes possible to grasp the target of treatment between the gripping pieces 15, 16. Here, one of the gripping pieces 15, 16 may be rotatably attach to the distal portion of the shaft 6, and both of the gripping pieces 15, 16 may be rotatably attached to the distal portion of the shaft 6. Further, a rod member (e.g., indicated by the reference numeral 10) to be inserted through the shaft 6 is provided; one of the gripping pieces 15 and 16 (e.g. the first gripping piece 15) may be formed from the protruding portion towards the distal side from the shaft 6 in the rod member (10). Furthermore, in the aforementioned embodiment, a rotation knob 17 is rotatably attached to the housing 5. As the rotary knob 17 rotates with respect to the housing 5, the shaft 6 and the end effector 7 rotate together with the rotary knob 17 about the central axis of the shaft 6 with respect to the housing 5.

To the housing 5, one end of a cable 13 is connected. The other end of the cable 13 is separably connected to the energy control device 3. An operation button 18 as energy operation input section (operation inputter) is attached the housing 5. By pressing the operation button 18, the operation to output electric energy from the energy control device 3 to the high-frequency treatment tool 2 is inputted to the energy control device 3. Note that instead of or in addition to the operation button 18, a foot switch or the like separate from the high-frequency treatment instrument 2 may be provided as the energy operation input section (operation inputter).

Figure 2:
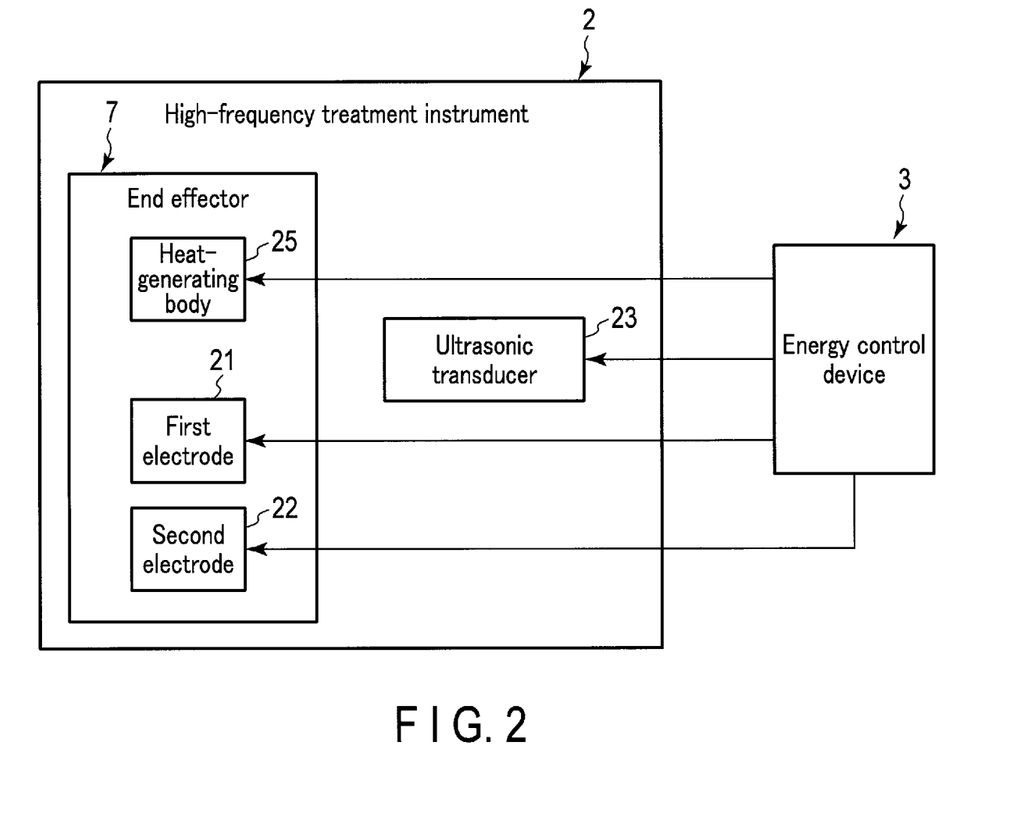
FIG. 2 is a block diagram schematically showing a configuration for supplying electric energy from an energy control device to a high-frequency treatment instrument according to the first embodiment.

FIG. 2 is a diagram showing a configuration for supplying electric energy from the energy control device 3 to the high-frequency treatment tool 2. As shown in FIG. 2, in the end effector 7, a first electrode 21 is provided in the first gripping piece 15 and a second electrode 22 is provided in the second gripping piece 16. The energy control device 3 includes an electric power source such as a battery or an outlet, a conversion circuit configured to convert electric power from the electric power source into electric energy to be supplied to the high-frequency treatment instrument, a controller such as a processor or an integrated circuit etc. including a CPU (Central Processing Unit) or an ASIC (Application Specific Integrated Circuit), and a storage medium. The energy control device 3 outputs, based on operation input with the operation button (energy manipulation input section) 18, high-frequency electric energy as electric energy. The high-frequency electric energy output from the energy control device 3 is supplied to the first electrode 21 and the second electrode 22 of the end effector 7. Due to the high-frequency electric energy being supplied, the pair of electrodes 21, 22 have electric potentials difference with respect to each other. As a result, a high-frequency current flows between the electrodes 21, 22 through the object of treatment being gripped, and a high-frequency current as treatment energy is applied to the target of treatment gripped between the gripping pieces 15, 16.

Note that, in an example, vibration-generating electric energy (alternating current electric power with a predetermined frequency) may be output in addition to the high-frequency electric energy from the energy control device 3. In this case, the ultrasonic transducer 23 is provided, for example, inside the housing 5 in the high-frequency treatment instrument 2, and the vibration-generating electric energy output from the energy control device 3 is supplied to the ultrasonic transducer 23. As a result, ultrasonic vibration is generated by the ultrasonic transducer 23. Furthermore, in the aforementioned example, the rod member (e.g., indicated by the reference numeral 10) as a vibration-transmitting member is inserted through the shaft 6, and the first gripping piece 15 is formed from the projecting portion of the rod member (10) which projects toward the distal side from the shaft 6. Therefore, the first gripping piece 15 (first electrode 21) is provided in the distal portion of the rod member (vibration-transmitting member). The rod member (10) resonates by transmitting the ultrasonic vibration generated by the ultrasonic transducer 23 from the proximal side to the distal side. Ultrasonic vibration causes the first gripping piece 15 (first electrode 21) of the end effector 7 to resonate, whereby ultrasonic vibration is applied as the treatment energy to the target of treatment being gripped.

In another example, heat-generating electric energy (direct current electric power or alternating electric power) may be output from the energy control device 3 in addition to the high-frequency electric energy. In this case, the heat-generating body 25 is provided, for example, in the end effector 7 (at least one of the gripping pieces 15, 16) of the high-frequency treatment instrument 2, and the heat-generating electric energy output from the energy control device 3 is supplied to the heat-generating body 25. As a result, heat is generated in the heat-generating body 25. For example, in the configuration in which the heat-generating body 25 is provided in the first gripping piece 15, the generated heat is transmitted to the target of treatment through the first electrode 21. In other words, the heat generated by the heat-generating body 25 is applied as the treatment energy to the target of treatment being gripped.

Figure 3:
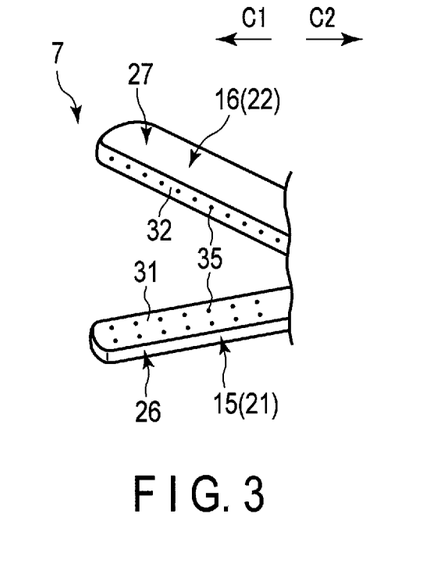
FIG. 3 is a schematic diagram showing a configuration of an end effector according to the first embodiment.

FIG. 3 is a diagram showing a configuration of the end effector 7. As shown in FIG. 3, the first electrode 21 has a first outer surface 26 exposed to the outside, and the second electrode 22 has a second outer surface 27 exposed to the outside. Each of the electrodes 21, 22 is made of metal such as titanium alloy or aluminum alloy, and has electric conductivity. The first outer surface 26 includes a first opposing surface 31 facing the second gripping piece 16 (second electrode 22). Further, the second outer surface 27 includes a second opposing surface 32 facing the first gripping piece 15 (first electrode 21). Whenever the target of treatment is gripped between the gripping pieces 15, 16, the target of treatment is sandwiched between the opposing surfaces 31, 32. Moreover, between the electrodes 21, 22, a high-frequency current is applied through the opposing surfaces 31, 32 to the target of treatment. This is to say that a high-frequency current flow is applied between the electrodes 21, 22 through the opposing surfaces 31, 32 to the target of treatment.

In the aforementioned embodiment, a coating (film) 35 covers the first opposing surface 31 on the first outer surface 26 of the first electrode 21, and a coating 35 covers the second opposing surface 32 on the second outer surface 27 of the second electrode 22. In other words, the coating 35 covers at least part of each of the outer surfaces 26, 27. The dotted hatching in FIG. 3 serves as the coating 35. Each of the electrodes 21, 22 serves as a base member of the coating 35.

Figure 4:
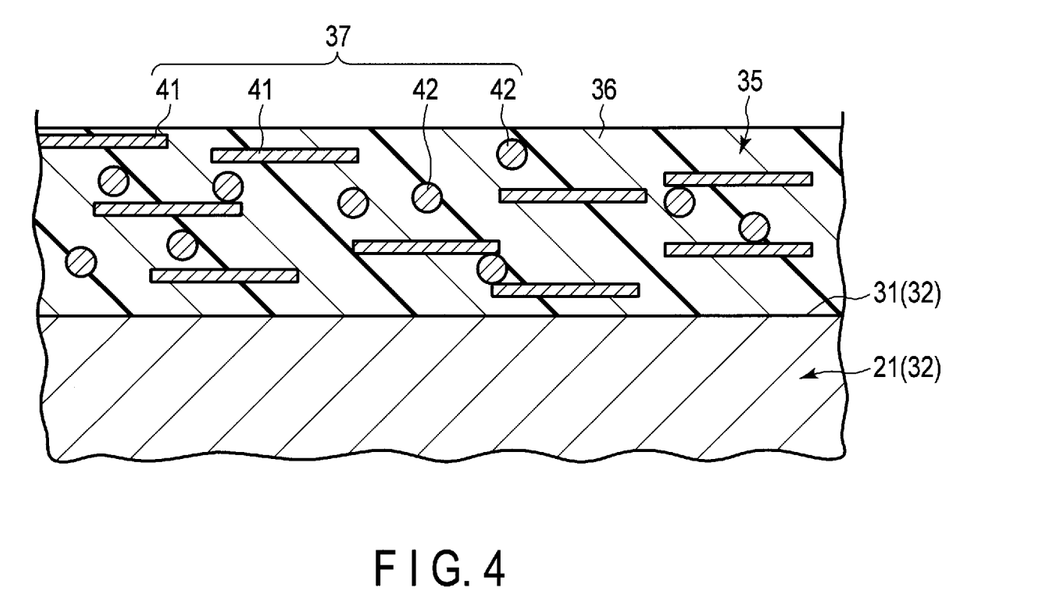
FIG. 4 is a cross-sectional view schematically showing a configuration of a coating according to the first embodiment.

FIG. 4 is a diagram showing a configuration of the coating 35. As shown in FIG. 4, the coating 35 is formed from a mixture of a non-conductive material 36 and a conductive material 37. The non-conductive material 36 includes both an electrically insulating material and a semiconductor material. In an example, the non-conductive material 36 contains a fluorine-based resin such as PTFE (polytetrafluoroethylene) or PFA (perfluoroalkoxyalkane) and PAI (polyamideimide). In this case, the fluorine-based resin, being a low-adhesive material to which body tissue does not easily adhere, is contained in the non-conductive material 36. In this manner, the target of treatment (biological tissue) is rendered less susceptible to adhering to the opposing surfaces 31, 32 covered by the coating 35, and the non-adhesiveness (releasability) is improved. In another example, either PEEK (polyetheretherketone) and silica (silicon dioxide), or PEEK and aerosol are contained in the non-conductive material 36. In this case, the heat-insulating property of the opposing surfaces 31, 32 covered by the coating 35 is improved. In yet another example, the non-conductive material 36 includes PEEK, and the abrasion resistance of the opposing surfaces 31, 32 covered by the coating 35 is improved. In other words, thanks to the non-conducting material 36, additional functions such as non-adhesiveness, thermal insulation or wear-resistance are added to the areas covered by the coating 35 on each of the outer surfaces 26, 27. Note that the non-conductive material 36 has at least one of the following additional functions: prevention of living tissue from adhering, water repellency, oil repellency, abrasion resistance, thermal insulation, additive coloration, anti-halation etc.

Furthermore, the conductive material 37 is copper, silver, or gold, and preferably silver. In the mixture for forming the coating 35, the volume percent of the conductive material 37 is smaller than the volume percent of the non-conductive material 36. Therefore, in the coating 35, the contact area between the non-conductive material 38 and the electrodes 21, 22 is larger than the contact area between the conductive material 37 and the electrodes 21, 22. In an example, the volume percent of the conductive material 37 of the mixture is 20% or less, preferably 15% or less (the volume percent of the non-conductive material 36 is preferably 85% or more).

The conductive material 37 contained in the mixture contains (a plurality (countless number) of) first elements 41, and (a plurality (countless number) of) second elements 42 each having a shape different from each of the first elements 41. In the aforementioned embodiment, the first elements 41 and the second elements 42 are a powder (particles) of the conductive material 37. Although preferably the first elements 41 and the second elements 42 are the same type of conductive material (e.g., aforementioned silver) with respect to each other, they may be different types of conductive materials with respect to each other. For example, in one example, the first elements 41 are silver and the second elements 42 are gold. All the (countless) first elements 41 may either be formed solely from the same type of conductive material, and the powder of these countless first elements 41 may be a mixture of different types of conductive materials (e.g., a mixture of silver and gold) with respect to each other. Likewise, all the (countless) second elements 42 may be formed solely from the same type of conductive material, and the powder of the countless second elements 42 may be a mixture of different types of conductive materials (e.g., a mixture of silver and gold) with respect to each other.

Figure 5:
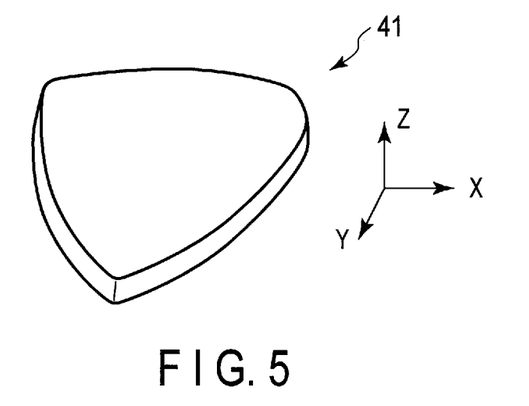
FIG. 5 is a perspective view schematically showing an example of a first element of a conductive material contained in the coating according to the first embodiment.
Figure 6:
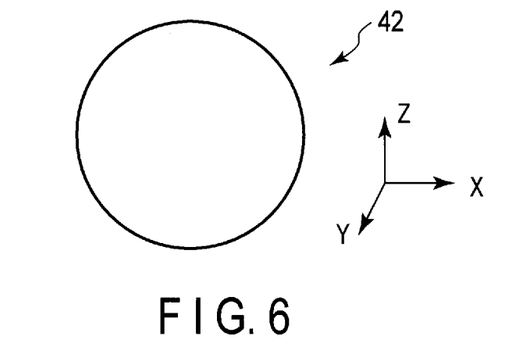
FIG. 6 is a perspective view schematically showing an example of a second element of a conductive material contained in the coating according to the first embodiment.
Figure 7:
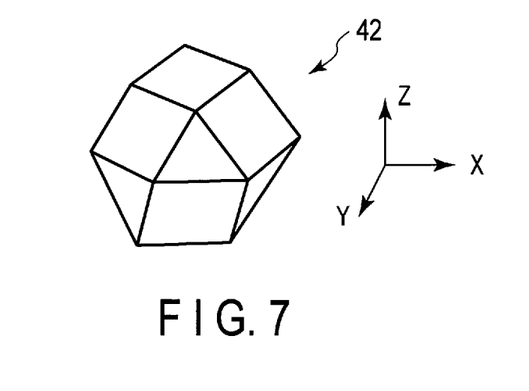
FIG. 7 is a perspective view schematically showing another example of the second element of the conductive material contained in the coating according to the first embodiment.
Figure 8:
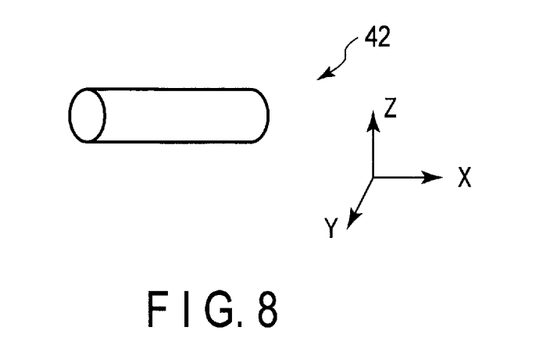
FIG. 8 is a perspective view schematically showing yet another example of the second element of the conductive material contained in the coating according to the first embodiment.

FIG. 5 is a diagram showing an example of the first element 41, and each of FIGS. 6-8 is a diagram showing an example of the second element 42. As shown in FIG. 5, each of the first elements 41 has a flat shape (flat form or oblate form). Thus, when defining in each of the first elements 41 three axes (X-, Y-, Z-axis) substantially perpendicular to each other, the dimension along one of the axes (for example, the Z-axis) is much smaller than the dimension along each of the other two axes (for example, the X- and Y-axis).

In an example (see FIG. 6), each of the second elements 42 is spherical (spherical form), and in another example (see FIG. 7), each of the second elements 42 has the shape of a polyhedron (polyhedron form). In these examples, when defining in each of the second elements 42 three axes (X-, Y-, Z-axis) substantially perpendicular to each other, the dimensions along the three axes (X-, Y-, Z-axis) have the same size with respect to one another. In another example (see FIG. 8), each of the second elements 42 has the shape of a line (line form) or fiber (fiber form). In this example, when defining in each of the second elements 42 three axes (X-, Y-, Z-axis) substantially perpendicular to each other, the dimension along one of the axes (for example, the X-axis) is much bigger than the dimension along each of the other two axes (for example, the Y- and Z-axis).

Since each of the first elements 41 and each of the second elements 42 has the aforementioned shape, the shape of each of the first elements 41 has a flatness quotient (flattening or oblateness) that is higher than each of the second elements 42. Furthermore, in the aforementioned embodiment, the volume percent of the first elements 41 in the mixture forming the coating 35 is smaller than the volume percent of the second elements 42. In an example, the volume percent of the second elements 42 in the mixture is about twice the volume percent of the first elements 41.

Next, the actions and effects of the high-frequency treatment instrument 2 of the aforementioned embodiment will be described. When treating a target of treatment such as living tissue using the treatment system 1 (high-frequency treatment instrument 2), the end effector 7 is inserted into a body cavity such as the abdominal cavity. The target of treatment is then placed between the gripping pieces 15, 16. In this state, the grip pieces 15, 16 are closed by the operation with the handle 12, so that the target of treatment is being gripped between the gripping pieces 15, 16. While the target of treatment is being gripped, a high-frequency electric energy is supplied from the energy control device 3 to the electrodes 21, 22 by performing the operation input with the operation button 18. As a result, a high-frequency current is applied through the opposing surfaces 31, 32 to the gripped target of treatment so as to be treated (coagulated). Note that at this point, as described above, a treatment energy other than the high-frequency current such as an ultrasonic vibration or heat may be applied to the target of treatment.

The coating 35 covering the opposing surfaces 31, 32 in the aforementioned embodiment is formed from a mixture of the non-conductive material 36 and the conductive material 37, wherein the conductive material 37 contains the first and second elements 41, 42 having different shapes with respect to each other. As a result of the coating 35 containing these two types of elements 41, 42 having the different shapes with respect to each other as the conductive material 37, a structure, in which the conductive material 37 is cross-linked in the coating 35 (see FIG. 4), is created. The structure with the cross-linked conductive material 37 ensures large electrostatic capacitance in the coating 35, even when the volume percent of the conductive material 37 in the mixture forming the coating 35 is small. In this manner, the impedance in the high-frequency current circuit passing through the coating 35 is reduced, even when the volume percent of the conductive material 37 in the coating 35 is small. Therefore, even when the volume percent of the conductive material 37 in the coating 35 is small, energization of the coating 35 is ensured. In other words, the coating 35 is made conductive.

Further, in the aforementioned embodiment, each of the first elements 41 is formed into a flat shape having a higher flatness quotient than each of the second elements 42. Since each of the first elements 41 has a shape with a high flatness quotient, the cross-link-structure of the conductive material 37 is easily formed in the coating 35. Moreover, the electrostatic capacitance of each of the first elements 41 having the shape with the high flatness quotient is increased. Thus, since each of the first elements has a shape with the high flatness quotient, the capacitance at the coating 35 is further increased, and the impedance in the circuit with the high-frequency current passing through the coating 35 is further reduced. In addition, by making the volume percent of the first elements 41 having the shape with a high flatness quotient smaller than the volume percent of the second elements 42 having the shape with a low flatness quotient, the cross-linked structure in the coating 35 is formed more easily, and the capacitance at the coating 35 is further increased.

Furthermore, since the conductivity of the coating 35 in the aforementioned embodiment, as described above, is ensured even when the volume percent of the conductive material 37 in the coating 35 is small, the volume percent of the conductive material 37 in the mixture forming the coating 35 is smaller than the volume percent of the non-conductive material 38. As the volume percent of the conductive material 37 in the coating 35 reduces, the strength of the coating 35 itself (i.e. film strength) is ensured. Moreover, in the coating 35, the contact area between the non-conductive material 38 and the electrodes 21, 22 is larger than the contact area between the conductive material 37 and the electrodes 21, 22. This effectively prevents the coating 35 from peeling off the opposing surfaces 31, 32 (electrodes 21, 22).

Moreover, since the volume percent of the non-conductive material 36 in the coating 35 is increased, additional functions such as non-adhesiveness, thermal insulation or wear resistance by the non-conductive material 36 are appropriately ensured. If, for example, a low-adhesive material, to which living tissue is less likely to adhere, is contained in the non-conductive material 36, the living tissue is effectively prevented on the opposing surfaces 31, 32 (portions of each of the outer surfaces 26, 27 covered by the coating 35) from adhering to the electrodes 21, 22.

(Modifications)

Figure 9:
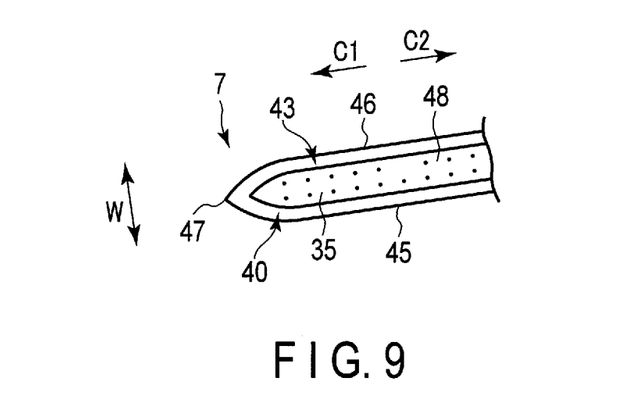
FIG. 9 is a schematic diagram showing a configuration of an end effector according to a modification.

Note that in the first embodiment, the end effector 7 includes a pair of gripping pieces 15, 16. However, it is not limited to this. For example, in a modification shown in FIG. 9, the end effector 8 is formed from a blade-shaped electrode 40. In this modification, the electrode 40 has an outer surface 43. On the outer surface 43 of the electrode 40, on the edge on one side in the width direction (direction of the arrow W), a first lateral blade 45 is formed, while on the edge on the other side in the width direction, a second lateral blade 46 is formed, and while on the edge on the distal side (the side indicated by the arrow C 1), a distal blade is formed. Moreover, on the outer surface 43 of the electrode 40, a first surface 48 facing one side in the thickness direction (direction perpendicular to the paper surface in FIG. 9) and a second surface (not shown) facing the side opposite to the first surface 48 are formed. In this modification, at least the first surface 48 is covered by the coating 35. In FIG. 9, the coating 35 is indicated by the dotted hatching.

In the aforementioned modification, the electrode 40 is provided in the vibration-transmitting member (10) which is inserted through the shaft 6, and by the ultrasonic vibration transmitted to the electrode 40, the electrode 40 resonates. By causing the electrode 40 to resonate while any one of the blades 45, 46, 47 is in contact with the target of treatment, the target of treatment is treated by the ultrasonic vibration.

While the first surface 48 of the electrode 40 in the aforementioned modification is in contact with the target of treatment, a high-frequency electric energy is being supplied from the energy control device 3 to the electrode 40 and a counter-electrode (not shown) disposed outside the body. In this manner, a high-frequency current flows between the electrode 40 and the counter-electrode through the first surface 48 (outer surface 43) of the electrode 40, the conductive coating 35 and the target of treatment, so that the high-frequency current is applied to the target of treatment.

As in the first embodiment, the coating 35 in the aforementioned modification is formed from a mixture of the non-conductive material 36 and the conductive material 37, wherein the conductive material 37 contains the first elements 41 and the second elements 42. In this manner, as in the first embodiment, conductivity and strength (film strength) of the coating 35 are ensured. Moreover, as in the first embodiment, in those portions where the coating 35 covers the outer surface 43 of the electrode 40, additional functions such as non-adhesiveness, thermal insulation or abrasion resistance by the non-conductive material 36 are appropriately ensured.

Also, in a modification, the end effector 7 may be formed from a hook-shaped (rake-shaped) electrode, and in another modification, the end effector 7 may be formed from a spatula-shaped electrode. In each of these cases, a high-frequency current likewise passes through the target of treatment between the electrode of the end effector 7 and the counter-electrode outside the body, so that a high-frequency current is applied to the target of treatment. Further, the outer surface of the electrode is covered by the aforementioned coating 35.

In the aforementioned embodiment etc., the high-frequency treatment instrument (2) includes the electrodes (21, 22; 40) having the outer surfaces (26, 27; 43), and as a result of the high-frequency electric energy supplied to the electrodes (21, 22; 40), a high-frequency current is applied through the outer surfaces (26, 27; 43) of the electrodes (21, 22; 40) to the target of treatment. The coating (35) covers at least part of the outer surfaces (26, 27; 43) of the electrodes (21, 22; 40), and is formed from the mixture obtained by mixing the non-conductive material (36) and the conductive material (37) so that the coating (35) is made conductive. The conductive material (37) contained in the mixture forming the coating (35) includes the first elements (41), and the second elements (42) each of which is different in shape from each of the first elements (41).

Additional advantages and modifications will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. A high-frequency treatment instrument comprising:
an end effector configured to treat a target of treatment, the end effector including:
an electrode having an outer surface, the electrode being configured to apply a high-frequency electric current to the target of treatment through the outer surface by being supplied with a high-frequency electric energy to the electrode, and
a coating covering at least part of the outer surface of the electrode, the coating being formed as a single layer from an integrated mixture of a non-conductive material and a conductive material forming the coating, the conductive material contained in the mixture being at a smaller ratio than the non-conductive material, the conductive material contained in the mixture including a plurality of first elements and a plurality of second elements, each of the plurality of first elements having a shape with a higher flatness quotient than a flatness quotient of each of the plurality of second elements, the plurality of first elements in the mixture being at a smaller ratio than the plurality of second elements so that the coating ensures large electrostatic capacitance and decreases impedance in circuits where the high-frequency current passes through, and thereby the coating is conductive with respect to the high-frequency current, and a contact area of distribution of the high-frequency energy through the coating between the non-conductive material and the electrode is larger than a contact area of distribution of the high-frequency energy through the coating between the conductive material and the electrode, while energizing the coating due to the electrostatic capacitance;
and a housing supporting the end effector, and the housing is configured to be held by an operator.

2. The high-frequency treatment instrument according to claim 1, wherein the plurality of first elements in the mixture is at a smaller ratio than the plurality of second elements so that the conductive material has a cross-linked structure, the coating increasing electrostatic capacitance by the cross-linked structure of the conductive material so that the coating decreases impedance in circuits where the high-frequency current passes through, and thereby the coating is conductive with respect to the high-frequency current.

3. The high-frequency treatment instrument according to claim 1, wherein each of the plurality of second elements has a spherical, a polyhedral or a linear shape.

4. The high-frequency treatment instrument according to claim 1, wherein each of the plurality of first elements and each of the plurality of second elements is a powder of the conductive material.

5. The high-frequency treatment instrument according to claim 1, further comprising a heat-generating body configured to generate heat and configured to transmit the generated heat through the electrode to the target of treatment.

6. The high-frequency treatment instrument according to claim 1, further comprising a vibration-transmitting member in which the electrode is provided, the vibration-transmitting member being configured to resonate when ultrasonic vibration is transmitted.

7. The high-frequency treatment instrument according to claim 1, wherein the non-conductive material has at least one of the following functions: prevention of living tissue from adhering, water repellency, oil repellency, abrasion resistance, thermal insulation, additive coloration, and anti-halation.

8. The high-frequency treatment instrument according to claim 1, wherein a volume percent of the plurality of second elements is twice a volume percent of the plurality of first elements.

9. An end effector comprising:
an electrode having an outer surface, the electrode being configured to apply a high-frequency electric current to the target of treatment through the outer surface by being supplied with a high-frequency electric energy to the electrode, and
a coating covering at least part of the outer surface of the electrode, the coating being formed as a single layer from an integrated mixture of a non-conductive material and a conductive material forming the coating, the conductive material contained in the mixture being at a smaller ratio than the non-conductive material, the conductive material contained in the mixture including a plurality of first elements and a plurality of second elements, each of the plurality of first elements having a shape with a higher flatness quotient than a flatness quotient of each of the plurality of second elements, the plurality of first elements in the mixture being at a smaller ratio than the plurality of second elements so that the coating ensures large electrostatic capacitance and decreases impedance in circuits where the high-frequency current passes through, and thereby the coating is conductive with respect to the high-frequency current, and a contact area of distribution of the high-frequency energy through the coating between the non-conductive material and the electrode is larger than a contact area of distribution of the high-frequency energy through the coating between the conductive material and the electrode, while energizing the coating due to the electrostatic capacitance.

10. The end effector according to claim 9, wherein the end effector is formed into forceps.

11. The end effector according to claim 9, wherein the end effector is formed into a surgical knife.

* * * * *